(12) United States Patent
Flachsmann

(10) Patent No.: US 9,585,362 B2
(45) Date of Patent: *Mar. 7, 2017

(54) FRAGRANCE COMPOUNDS

(71) Applicant: Givaudan, S.A., Vernier (CH)

(72) Inventor: Felix Flachsmann, Duebendorf (CH)

(73) Assignee: Givaudan S.A., Vernier (CH)

( * ) Notice: Subject to any disclaimer, the term of this patent is extended or adjusted under 35 U.S.C. 154(b) by 0 days.

This patent is subject to a terminal disclaimer.

(21) Appl. No.: 15/185,226

(22) Filed: Jun. 17, 2016

(65) Prior Publication Data

US 2016/0286753 A1 Oct. 6, 2016

Related U.S. Application Data

(60) Continuation-in-part of application No. 14/714,693, filed on May 18, 2015, now Pat. No. 9,447,364, which is a division of application No. 14/041,053, filed on Sep. 30, 2013, now Pat. No. 9,057,041, which is a division of application No. 12/304,224, filed as application No. PCT/CH2007/000294 on Jun. 13, 2007, now Pat. No. 8,575,386.

(30) Foreign Application Priority Data

Jun. 15, 2006 (GB) .................................. 0611770.9

(51) Int. Cl.
C11D 3/50 (2006.01)
A01K 1/015 (2006.01)

(52) U.S. Cl.
CPC .......... *A01K 1/0155* (2013.01); *A01K 1/0152* (2013.01)

(58) Field of Classification Search
CPC ....... C11D 3/50; C11D 3/2072; C07C 69/533; C07C 49/255; C07C 45/74; C11B 9/0007
See application file for complete search history.

(56) References Cited

U.S. PATENT DOCUMENTS

| 3,558,659 A | 1/1971 | Julia |
| 3,655,620 A | 4/1972 | Julia |
| 3,761,505 A | 9/1973 | Julia |
| 3,789,797 A | 2/1974 | Brewer |
| 4,437,429 A | 3/1984 | Goldstein et al. |
| 4,808,747 A | 2/1989 | Homann |
| 5,415,854 A | 5/1995 | Forestier et al. |
| 9,057,041 B2 * | 6/2015 | Flachsmann ............ C07C 45/74 |
| 9,447,364 B2 * | 9/2016 | Flachsmann ............ C07C 45/74 |

FOREIGN PATENT DOCUMENTS

| DE | 2335067 A1 | 1/1974 |
| DE | 4101737 A1 | 8/1974 |
| EP | 0168563 A2 | 1/1986 |
| FR | 2642967 A | 8/1990 |
| FR | 2818144 A | 6/2002 |
| GB | 857163 A | 12/1960 |
| GB | 1420802 A | 1/1976 |
| IN | 73702 A | 10/1960 |
| JP | 62226934 A | 10/1987 |
| JP | 07331278 A | 12/1995 |
| WO | WO 2006076821 A | 7/2006 |

OTHER PUBLICATIONS

Adlington, Robert M., et al: "Towards a biomimetic synthesis of the marine alkaloids papuamine and haliclonadiamine model studies"; STN Database accession No. 2000:97388 abstract, 2000; Database CA [Online], Chemical Abstracts Service, Columbus, OH, US.

Anrade, Carlos Kleber Z., et al: "Intramolecular ene reactions catalyzed by NbC15, TaC15 and InC13"; STN Database accession No. 2005:38385 abstract, 2004; Database CA [Online], Chemical Abstracts Service, Columbus, OH, US.

Armesto, Diego, et al: "Novel Oxa-di-.pi.-methane and Norrish Type I Reactions in the S2 (.pi., .pi.*) Excited State of a Series of .beta., gamma.-Unsaturated Keytones"; STN Database accession No. 2005:436093 abstract, 2005; Database CA [Online], Chemical Abstracts Service, Columbus, OH, US.

Cardillo, Giuliana, et al: "Synthesis of Aziridine-2, 2-dicarboxylates via 1,4-Addition of N,0-(Bistrimethylsilyl)hydroxylamine to .alpha.,.beta.-Unsaturated Malonates"; STN Database accession No. 2001:836862 abstract, 2001; Database CA [Online], Chemical Abstracts Service, Columbus, OH, US.

Chen, Chen, et al: "Studies of the application of elementoorganic compounds of Groups 15 and 16 in organic synthesis. Part 70. Tributylstibine-mediated olefination of carbonyl compounds with bromomalonic ester and with dibromomalonic ester. A possible pathway through a stibonium ylide via halophilic initiation by terti"; STN Database accession No. 1991:24057 abstract, 1990; Database CA [Online], Chemical Abstracts Service, Columbus, OH, US.

(Continued)

*Primary Examiner* — Sudhakar Katakam
(74) *Attorney, Agent, or Firm* — Curatolo Sidoti Co., LPA; Joseph G. Curatolo; Salvatore A. Sidoti

(57) ABSTRACT

A method of providing a fragrant odour to an application, comprising the addition thereto of at least one compound of the formula I

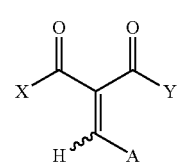

I wherein X and Y are independently selected from the group consisting of —CR$^1$R$^2$R$^3$, —NR$^4$R$^5$ and —OR$^6$, wherein R$^1$ to R$^5$ are selected from H and essentially hydrocarbon moieties that optionally comprise at least one oxygen, nitrogen or silicon atom, and R$^6$ is selected from essentially hydrocarbon moieties that optionally comprise at least one oxygen, nitrogen or silicon atom; and, A is an essentially hydrocarbon moiety that optionally comprises at least one oxygen, sulphur, nitrogen or silicon atom, with the proviso that the compound A-CHO is a fragrant aldehyde. The use of these compounds in laundry, household and personal care products confers a long-lasting freshness.

11 Claims, No Drawings

(56) References Cited

OTHER PUBLICATIONS

Corey, E. J., et al: "A new enantiospecific route to the pseudopterosins"; STN Database accession No. 1990:631724 abstract, 1990; Database CA [Online], Chemical Abstracts Service, Columbus, OH, US.

Doleschall, Gabor et al: "Synthesis of diethyl alkylidenemalonates by the reduction of C-acylmalonic diethyl esters"; STN Database accession No. 1992:173539 abstract, 1991; Database CA [Online], Chemical Abstracts Service, Columbus, OH, US.

Herrmann, W. A., et al: "Multiple bonding between Main Group elements and transition metals. 100. Part 3. A new aldehyde olefination with methyltrioxorhenium as catalyst"; STN Database accession No. 1992:105587 abstract, 1991; Database CA [Online], Chemical Abstracts Service, Columbus, OH, US.

Hiramatsu, Hideo, et al: "The Knoevenagel reaction of aldehydes with active methylene compounds having keto-enoltautomerism"; STN Database accession No. 1989:533733 abstract, 1989; Database CA [Online], Chemical Abstracts Service, Columbus, OH, US.

Jeon, Hye-Sun, et al: "Preparation of the conjugated polyene chains with the 1,4-dimethyl substitution"; STN Database accession No. 2004:706941 abstract, 2004; Database CA [Online], Chemical Abstracts Service, Columbus, OH, US.

Journal Fuer Praktische Chemie, 1918, vol. 97, Knoevenagel, pp. 288-355.

Kasatkin, A. N., et al: "Reactions of some CH-acid titanium derivatives with carbonyl compunds. IV. Synthesis and some transformations of (2-alkenylidene)malonic acid derivatives"; STN Database accession No. 1991:655595 abstract, 1991; Database CA [Online], Chemical Abstracts Service, Columbus, OH, US.

Kasatkin, A. N., et al: "Trphenyl[5,5-bis(ethoxycarbonyl)-2,4-pentadienylidene]phosphorane and its condensation reactions"; STN Database accession No. 1991:583453 abstract, 1991; Database CA [Online], Chemical Abstracts Service, Columbus, OH, US.

Kryshtal, G. V., et al: "Reactions of CH-acids with .alpha.,.beta.-unsaturated aldehydes in ionic liquids"; STN Database accession No. 2004:589868 abstract, 2004; Database CA [Online], Chemical Abstracts Service, Columbus, OH, US.

Liao, Yi, et al: "Synthetic application organometallic compounds of groups 15 and 16. 86. A novel olefination of diazo compounds with carbonyl compounds mediated by tributylstibine and a catalylitic amount of copper(I) iodine"; STN Database accession No. 1991:120956 abstract, 1990; Database CA [Online], Chemical Abstracts Service, Columbus, OH, US.

Nigmatov, A.G.., et al: "Mechanism of cyclocondensation reaction between acyclic isopenoidal .alpha.,.beta.-enals and monoethyl malonate under Knoevengal reaction conditions"; STN Database accession No. 1991:514789 abstract, 1991; Database CA [Online], Chemical Abstracts Service, Columbus, OH, US.

Okauchi, Tatsuo, et al: "Lewis Acid-Catalyzed Intramolecular [2+2] Cycloaddition of .alpha.-Ester-Substituted Conjugated Dienyl- and Trienylphosphonates. New Synthesis of Functionalized Cyclic Terpenoids"; STN Database accession No. 1997:724058 abstract, 1997; Database CA [Online], Chemical Abstracts Service, Columbus, OH, US.

Snider, Barry B., et al: "Synthesis of the tricyclic portions of batzelladines A, B and D. Revision of the stereochemistry of batzelladines A and D"; STN Database accession No. 1996:605681 abstract, 1996; Database CA [Online], Chemical Abstracts Service, Columbus, OH, US.

Sutherland, Andrew J., et al: "Synthesis of C-D-ring analogs of the azasteroid A25822"; STN Database accession No. 1996:126244 abstract, 1996; Database CA [Online], Chemical Abstracts Service, Columbus, OH, US.

Tietze, L. F., et al: "Diastereoselective formation of trans-1,2-disubstituted cyclohexanes from alkylidenemalonates by an intramolecular ene reaction: dimethyl (1'R,2'R,5'R)-2-(2'-isopropenyl-5'-methylicyclohex-1'yl)-propane-1,3-dioate"; STN Database accession No. 1994:509285 abstract, 1993; Database CA [Online], Chemical Abstracts Service, Columbus, OH, US.

Tietze, L. F., et al: "Intramolecular ene reactions. 7. Asymmetric induction in intramolecular ene reactions of chiral 1,7-dienes: a diastereo- and enantioselective synthesis of substituted cyclohexanes"; STN Database accession No. 1989:423107 abstract, 1989; Database CA [Online], Chemical Abstracts Service, Columbus, OH, US.

Tietze, L. F., et al: "New and efficient Lews acid catalysts in intramolecular ene reactions"; STN Database accession No. 1989:423729 abstract, 1988; Database CA [Online], Chemical Abstracts Service, Columbus, OH, US.

Tolstikov, G. A., et al: "Prostanoids. XXXI. Levuglandin analogs. Construction of the latent form of the .gamma.-ketoaldehyde section"; STN Database accession No. 1990:590976 abstract, 1990; Database CA [Online], Chemical Abstracts Service, Columbus, OH, US.

Tolstikov, G. A., et al: "Prostanoids. XXXIV. Cyclic analogs of levuglandins. Structure of the allylic alcohol side chain"; STN Database accession No. 1991:607701 abstract, 1990; Database CA [Online], Chemical Abstracts Service, Columbus, OH, US.

Tsuno, Takashi, et al: "Allenyl(vinyl)methane photochemistry. Photochemistry of .gamma.-allenyl-substituted .alpha.,.beta.-unsaturated enone derivatives"; STN Database accession No. 2002:6757344 abstract, 2002; Database CA [Online], Chemical Abstracts Service, Columbus, OH, US.

Tsuno,Takashi, et al: "Allenyl(vinyl)methane photochemistry. Photochemistry of Methyl 4, 4-Dimethyl-2,5,6-heptatrienoate Derivatives"; STN Database accession No. 1999:162715 abstract, 1999; Database CA [Online], Chemical Abstracts Service, Columbus, OH, US.

Zhou, Zhanglin, et al: "Synthetic application of elemento-organic compounds of Groups 15 and 16. 89. A novel olefination of carbonyl compounds with dibromomalonate promoted by dibutyl telluride"; STN Database accession No. 1991:514319 abstract, 1991; Database CA [Online], Chemical Abstracts Service, Columbus, OH, US.

British Search Report, GB 0611770.9, (Oct. 12, 2006).

International Search Report, PCT/CH2007/000294, mailed Sep. 17, 2007.

Written Opinion, PCT/CH2007/000294, mailed Sep. 17, 2007.

* cited by examiner

FRAGRANCE COMPOUNDS

The present application is a continuation-in-part of co-pending U.S. Ser. No. 14/714,693, filed May 18, 2015, which is a division of U.S. Ser. No. 14/041,053, filed Sep. 30, 2013, now U.S. Pat. No. 9,057,041, issued Jun. 16, 2015, which is a division of U.S. Ser. No. 12/304,224, filed on Dec. 10, 2008, now U.S. Pat. No. 8,575,386, issued Nov. 5, 2013, which is a national stage application of International Patent Application No. PCT/CH2007/000294, filed Jun. 13, 2007, which claims the benefit of British Patent Application No. GB 0611770.9, filed Jun. 15, 2006, which applications are incorporated herein by reference.

This invention relates to the provision of fragrance and to a process and compounds for achieving this. More particularly, the present disclosure relates to compounds which can be used in a variety of products to reduce odours caused by animal urine or feces, especially those of domestic pets.

The provision of fragrance by the addition of inherently fragrant substances to products is well known and widely used. An alternative method of providing fragrance is by the use of a precursor, that is, a substance that is not itself fragrant, but which, in particular circumstances, for example exposure to light, pH change and enzymatic activity, will break down to give at least one fragrant substance.

It has now been discovered that a particular class of substances can act as precursors by providing a source of at least one fragrant aldehyde. The invention therefore provides a method of providing a fragrant odour to an application, comprising the addition thereto of at least one compound of the formula I

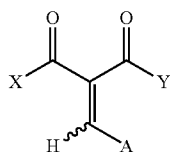

wherein

X and Y are independently selected from the group consisting of —$CR^1R^2R^3$, —$NR^4R^5$ and —$OR^6$, wherein $R^1$ to $R^5$ are selected from H and essentially hydrocarbon moieties that optionally comprise at least one oxygen, nitrogen or silicon atom, and $R^6$ is selected from essentially hydrocarbon moieties that optionally comprise at least one oxygen, nitrogen or silicon atom; and A is an essentially hydrocarbon moiety that optionally comprises at least one oxygen, sulphur, nitrogen or silicon atom, with the proviso that the compound A-CHO is a fragrant aldehyde.

The invention additionally provides use of a compound of Formula I as hereinabove defined as a precursor of a fragrance.

By "essentially hydrocarbon moieties that optionally comprise at least one oxygen, nitrogen or silicon atom" (and, in the case of A, also at least one sulphur atom) is meant that the moieties X, Y and A are at least predominantly hydrocarbon in nature, that is, that the moieties will comprise mainly carbon and hydrogen, and that the number of carbon atoms present on a given moiety is greater than that of any oxygen, nitrogen and silicon (and, in the case of A, sulphur) atoms present. Thus, if there is present one oxygen atom, there must be present at least two carbon atoms on the moiety. The oxygen, nitrogen, sulphur and silicon atoms may either form part of the otherwise hydrocarbon chain, or they may be linked to carbon atoms on the chain, either directly (for example, a carbonyl group oxygen or a hydroxyl group) or as part of a substituent (for example, a nitrile group).

The wavy bond to the hydrogen means that the arrangement at the ethylenic double bond may be either in the E- or the Z-configuration. In individual instances, depending on the natures of X and Y, one or other isomer may be preferred, but this is not usually the case. With regard to X and Y, there may be present stereogenic units such as chiral centres or substituted double bonds, which result in there existing several different stereoisomers. In some cases, these can result in odours of different strengths or even characters, and these can be separated by conventional techniques, if desired. However, this adds to the complexity (and therefore the expense), and it is generally preferred to leave the compounds as a mixture of stereoisomers.

A is defined by the requirement that A-CHO is a fragrant aldehyde. Such molecules are well known to the art. Examples of fragrant aldehydes from which the moiety A may be derived include, but are not limited to, the following:

2,6,10-trimethylundec-9-enal,
8,8-dimethyl-1,2,3,4,5,6,7,8-octahydro-naphthalene-2-carbaldehyde,
(4-isopropyl-phenyl)-ethanal,
2,4-dimethyl-cyclohex-3-ene-1-carbaldehyde,
1,3,5-trimethyl-cyclohex-1-ene-4-carbaldehyde,
4-(4-hydroxy-4-methylpentyl)-cyclohex-3-ene-1-carbaldehyde,
hex-2-enal,
3,5,5-trimethyl-hexanal,
heptanal,
2,6-dimethyl-hept-5-enal,
decanal,
dec-9-enal,
dec-4-en-1-al,
2-methyl-decanal,
undec-10-en-1-al,
undecanal,
dodecanal,
2-methyl-undecanal,
tridecanal,
tridec-2-enal,
octanal,
nonanal,
non-2-enal,
undec-9-enal,
2-phenyl-propanal,
2-(4-methyl-phenyl)-ethanal,
3,7-dimethyl-octanal,
dihydrofarnesal,
7-hydroxy-3,7-dimethyl-octanal,
2,6-dimethyl-oct-5-en-1-al,
3-(3-isopropyl-phenyl)-butanal
2-(3,7-dimethyl-oct-6-en-oxy)-ethanal,
4-(4-methyl-pent-3-enyl)-cyclohex-3-ene-1-carbaldehyde,
2,3,5,5,-tetramethyl-hexanal,
longifolic aldehyde,
2-methyl-4-(2,6,6-trimethylcyclohex-2-en-1-yl)-butanal,
2-methyl-3-(4-tert-butylphenyl)-propanal,
3-(4-tert-butyl-phenyl)-propanal,
2-(4-isopropyl-phenyl)-propanal,
3-(benzo[1,3]dioxol-5-yl)-2-methyl-propanal,
3,7-dimethyl-oct-6-ene-1-al,
2-methyl-3-(4-isopropylphenyl)-propanal, 4-tert-butyl-cyclohexane-1-carbaldehyde,
4-(octahydro-4,7-methano-5H-inden-5-ylidene)-butanal,
(3,7-dimethyl-oct-6-enyloxy)-ethanal,
(2E,6Z)-nonadienal,
2,4-dimethyl-2,6-heptadienal,
(E)-dec-2-enal,
dodec-2-enal,
3,7-dimethyl-octa-2,6-dienal,
2,4-diethyl-hepta-2,6-dienal,
3,7-dimethyl-nona-2,6-dienal,
3-propyl-hept-2-enal, and
4-isopropenyl-cyclohex-1-ene-1-carbaldehyde.

In particular embodiments, X and Y are independently selected from the following moieties:

(a) $C_1$-$C_{20}$ alkyl, linear or branched, optionally containing oxygen, nitrogen or silicon atoms, such as methyl, ethyl, propyl, butyl, isobutyl, 2-ethylhexyl, tert.-butyl;

(b) cyclopropyl, cyclopentyl, cyclohexyl, cyclooctyl; optionally containing oxygen, nitrogen or silicon atoms, such as tetrahydrofuranyl, pyranyl, piperidinyl, pyrrolidinyl;

(c) $C_4$-$C_{20}$ alkylcycloalkyl, optionally containing oxygen, nitrogen or silicon atoms, such as methylcyclohexyl, ethylcyclohexyl, methylcyclopentyl;

(d) $C_6$-$C_{20}$ cycloalkylalkyl optionally containing oxygen, nitrogen or silicon atoms, such as (4-methyl)-cyclohexyl, (e) $C_3$-$C_{10}$ alkenyl, linear or branched, optionally containing oxygen, nitrogen or silicon atoms, such as propenyl, isopropenyl, isobutenyl;

(f) $C_6$-$C_{10}$ aryl with optional substituents, such as phenyl, o- or p-methoxyphenyl;

(g) $C_7$-$C_{10}$ alkylaryl with optional substituents and containing optionally oxygen, nitrogen or silicon atoms, such as benzyl, methoxybenzyl;

(g) $C5$-$C_{10}$ heteroaryl, such as pyridinyl, furanyl, pyrryl, imidazolyl;

(h) —$OR^6$, wherein $R^6$ is $C_1$-$C_{20}$ alkyl, linear or branched, optionally containing oxygen, nitrogen or silicium atoms, such as methyl, ethyl, propyl, butyl, isobutyl, 2-ethylhexyl, tert.-butyl; or cyclopentyl, cyclohexyl; or $C_3$-$C_{10}$ alkenyl, linear or branched, such as propenyl, isopropenyl, isobutenyl; or $C_6$-$C_8$ aryl, such as phenyl or naphtyl; and (i) —$NR^4R^5$, wherein $R^4$ and $R^5$ are, independently of each other, H; $C_1$-$C_{20}$ alkyl, linear or branched, such as methyl, ethyl, propyl, butyl, isobutyl, 2-ethylhexyl, optionally containing oxygen or nitrogen atoms; or cyclopentyl, cyclohexyl; alternatively $NR^4R^5$ form together a 3-, 5- or 6-membered ring;

and

A is selected from the group consisting of $C_7$-$C_{17}$ linear or branched alkyl, cycloalkyl, alkylcycloalkyl or cycloalkylalkyl, $C_7$-$C_{15}$ linear or branched alkenyl, and $C_6$-$C_{10}$ aryl.

One way of preparing the compounds is via a Knoevenagel condensation, in which a fragrant aldehyde is reacted with a suitable 1,3-dicarbonyl compound in the presence of a suitable catalyst, such as secondary amines, for example, piperidine, pyrrolidine, dimethylamine, diethylamine, or ammonium salts, for example, ammonium acetate and ethylene diamine diacetate. Many other catalysts do promote this reaction and are known to the person skilled in the art of organic synthesis. The reaction is depicted schematically below:

As the groups X and Y of the 1,3-dicarbonyl compound play no part in the reaction, the compound may be chosen from a very wide variety of such materials. Specific examples of 1,3-dicarbonyl compounds include ethyl 3-oxobutanoate, ethyl 3-oxo-3-phenylpropanoate, benzyl 3-oxobutanoate, diethyl malonate, dimethyl malonate, diisopropyl malonate, dibenzyl malonate, 1-(4-tert-butylphenyl)-3-(4-methoxyphenyl)-propane-1,3-dione (Parsol™ 1789) and ethyl 1-(3,3-dimethylcyclohexyl)ethyl malonate (Musk Nouvelle™, (IFF)).

Specific examples of compounds include the following:

-continued (v), (vi), (vii), (viii), (ix), (x), (xi), (xii), (xiii), (xiv), (xv), (xvi), (xvii), (xviii)

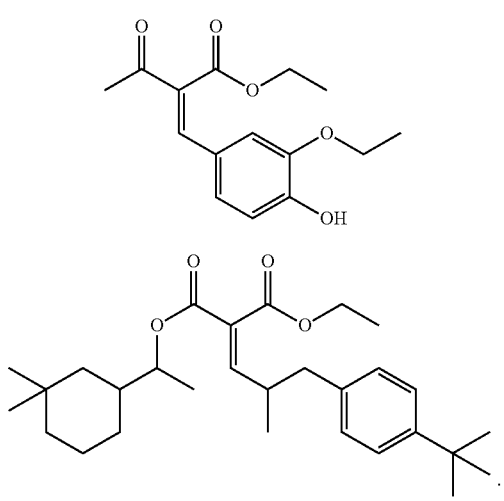

While some of these compounds are known (but not for this particular purpose), others are novel. For example, in the formulae depicted above, Nos. (iv), (v), (vii), (xi)-(xxvii) and (xx) are novel. The invention therefore also provides a compound of the formula I

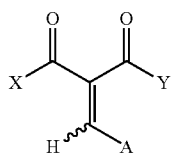

wherein
i) X and Y are the same and are selected from
a) —OR$^6$, wherein R$^6$ is selected from the group consisting of methyl, ethyl, propyl, isopropyl, butyl, isobutyl, t-butyl, benzyl; or
b) phenyl, methyl, ethyl, propyl, isopropyl, butyl, isobutyl ;
or
ii) X and Y are different, and are selected according to the following table:

| X | Y |
|---|---|
| Me | OMe, OEt, O—tBu, O—iPr, OBn, O-cis-3-hexenyl |
| Me | Et, Pr, Bu, Pent |
| Ph | OMe, OEt |
| 2-(1-(3,3-dimethyl-cyclohexyl)ethoxy | OEt | and;

A is selected from branched or linear $C_7$-$C_{15}$ alkyl and $C_7$-$C_{15}$ alkenyl moieties, these optionally comprising oxygen atoms present as ether, hydroxyl, carbonyl or ester moieties.

All of the compounds of formula I hereinabove described have in common the fact that, on exposure to moisture, either liquid water applied to the compounds or to a support on which they have been deposited, or water vapour in the atmosphere, they release a fragrant aldehyde.

As previously mentioned, the groups X and Y of the 1,3-dicarbonyl compound

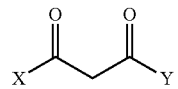

play no part in the reaction, and they may be chosen from a very wide variety of such materials. However, in a further aspect of the invention, they can be chosen such that the compound, once separated from the fragrant aldehyde, performs a desired function. For example, the compound itself may have fragrant characteristics, either as a fragrant material in its own right, or as a modifier for the fragrant aldehyde, or other fragrant material also present in a composition in which the compound useful in the invention is used. Another possibility is that it may enhance substantivity or stability in a given application. A third possibility is that it perform an entirely independent function in a composition. For example, it may act as a sunscreen, thus, for example, supplying a cosmetic composition simultaneously with a fragrance and a protective function. The skilled person will readily comprehend that there are many other possible uses, and will be able to tailor the 1,3-dicarbonyl compound appropriately to perform any such function.

The invention is useful for providing a fragrant odour to an application where release of the odour is desired at some particular time point and is caused by the presence of moisture. "Application" in the context of this invention means any use in which such an effect is desired. Examples include laundry use (release in a wash liquor, in a dryer or on laundry post-drying), use in hard surface cleaners, cosmetics, protective creams, personal care products, such as hair care products, skin creams and lotions, fine fragrances and air-care products, such as air fresheners.

In use, the compounds may be combined with any other suitable free fragrance material. For example, they may be combined with free fragrance aldehydes, so that the free fragrance delivers an immediate impact and the compounds of the invention provide a lasting fragrance. By using the compounds of the present invention, the strong floral-fresh impact of many fragrant aldehydes, which by themselves are not substantive, can be prolonged in many applications where such long-lasting freshness is desired, without having to overdose the aldehydes in the perfume. This opens new possibilities for fragrance creation.

The compounds for use in this invention may be incorporated into commercial products in conventional proportions and by art-recognised methods. Commercial products include washing and laundry detergents, fabric softeners and conditioners, personal care products, such as hair and skin care preparations, soaps and lotions. Additional products include animal litter, such as pet litter. They may be incorporated directly into such compositions, or they may be added in conjunction with a carrier, such as microcapsules, adsorbed on to suitable particulate matter or spray-dried.

One of the particular features of this invention is that, if the Knoevenagel synthesis hereinabove described is used, the compounds need not be made in a manufacturing plant and shipped to the user, but they may be made in situ. They can thus be made simply and easily on site and then added directly to the composition in which their presence is desired. This confers a considerable versatility, in that it allows a user to make a desired compound on the spot, without waiting for a delivery. The invention therefore also provides a process of manufacturing a fragranced composition, in which the fragrance is gradually released on exposure to moisture, comprising the steps of
(a) blending a compound of the formula II

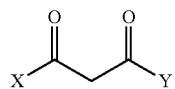

wherein X and Y are as hereinabove defined, with a fragrant aldehyde in the presence of a base under such conditions that a Knoevenagel condensation takes place; and (b) adding the product of (a) to the composition.

Conditions allowing a Knoevenagel condensation to take place in situ, i.e. step a) in the above-described process, include also thermal dehydration methods such as spray-drying. Therein, the mixture of a compound of formula II, together with one or several fragrant aldehydes and a base are formulated into an aqueous emulsion, containing optional carrier materials and surfactants. This emulsion is then spray-dried, thereby producing solid particles containing products of formula I.

Pet Litter

The increase in animal pet population has led to an increasing usage of animal litter materials. There are numerous animal litter products available commercially and taught by the prior art. They are usually based on inexpensive materials such as abundant natural minerals e.g. sand, granulated clays or zeolite, or recycled waste cellulosic materials such as woodchips, sawdust, shredded paper, pelleted or shredded recycled cloth, ground wood bark, alfalfa or other vegetable matter such as ground corn husk. In order to improve the performance of animal litters additional materials are added to improve absorbency, to clump the particles, to ease disposal and odour treatment agents. U.S. Pat. No. 4,437,429 teaches using zeolite to control odours in clay based litter. U.S. Pat. No. 3,789,797 combines bentonite clay with alfalfa which supplies chlorophyll as a deodorizer. Fragrance compounds according to the present disclosure can either be incorporated into the pet litter during manufacture or added later in use.

In one embodiment, fragrance compounds may be present in the pet litter at an effective level to provide a reduced urine malodour effect, typically from about 0.05% to about 5% and in another embodiment, from about 0.1% to about 0.5%, by weight of the litter material. In another embodiment, the fragrance compounds according to the present disclosure may be placed into a spray dispenser in order to be distributed onto the desired area, for example, pet litter. In another embodiment, the fragrance compounds may be packaged in a consumer product in association with instructions to apply to pet litter, or other surfaces having animal odour to reduce the malodour impression.

The invention is now further described with reference to the following non-limiting examples, which describe preferred embodiments.

EXAMPLE 1

Preparation of 2-benzoyl-dec-2-enoic acid ethyl ester, a compound according to the formula

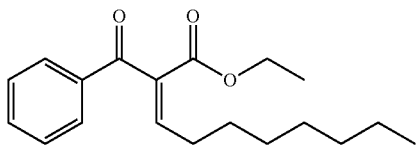 [SMILES: CCCCCCC/C=C(\C(=O)OCC)C(=O)c1ccccc1]

Piperidine (0.10 ml, 0.5 mol %) is added to a mixture of octanal (25.6 g, 0.20 mol) and ethyl benzoylacetate (38.4 g, 0.20 mol) at 5° C. The resulting solution is warmed to room temperature and stirred for 24 h, during which a fine emulsion is formed. The mixture is diluted with methyl t-butyl ether and the organic layer washed with 2 N aq. HCl-solution, water and brine, then dried over $MgSO_4$.

The solvent is removed in vacuo and the residue distilled to yield 18.0 g (38%) of product as an E/Z-mixture, boiling at 129-135° C./0.1 mbar.

$^{13}$C-NMR ($CHCl_3$, 100 MHz; main isomer): 194.5 (s), 164.6 (s), 148.6 (d), 137.2 (s), 133.7 (d), 133.6 (s), 129.0 (d), 128.8 (d), 61.0 (t), 31.6 (t), 29.5 (t), 29.1 (t), 28.8 (t), 28.3 (t), 22.5 (t), 14. (q), 13.9 (q).

MS (EI, 70 eV): 302 (<1, M$^+$), 257 (2), 217 (10), 199 (15), 186 (15), 171 (4), 157 (13), 105 (100).

EXAMPLES 2-12

The following compounds are made by a method according to claim 1, using the appropriate fragrant aldehyde and 1,3-dicarbonyl compound:

| N° | Structure | b.p. (if distilled) [° C./mbar] | $^{13}$C-NMR CDCl$_3$, 100 MHz (only main isomer) | MS EI, 70 eV |
|---|---|---|---|---|
| 2 | 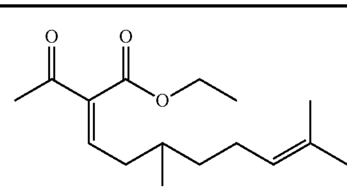 | 127/0.07 | 194.9 (s), 166.5 (s), 147.5 (d), 139.8 (s), 131.6 (s), 124.2 (d), 59.4 (t), 39.5 (t), 35.3 (t), 32.3 (d), 27.4 (t), 25.7 (q), 22.4 (q), 19.6 | 266 (29, M$^+$), 221 (27), 205 (26), 177 (29), 149 (20), 43 |

-continued

| N° | Structure | b.p. (if distilled) [° C./mbar] | $^{13}$C-NMR CDCl$_3$, 100 MHz (only main isomer) | MS EI, 70 eV |
|---|---|---|---|---|
| 3 | 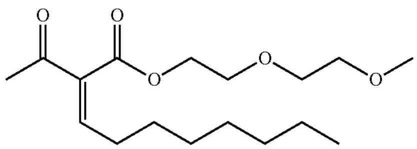 [SMILES: CCCCCCC/C=C(/C(C)=O)C(=O)OCCOCCOC] | 168-171° C./ 0.08 | 195.0 (s), 168.8 (s), 149.3 (d), 136.6 (s), 71.8 (t), 70.4 (t), 68.9 (t), 63.5 (t), 58.9 (q), 32.5 (t), 30.0 (t), 29.2 (t), 29.0 (t), 27.0 (t), 22.5 (t), 27.0 (q), 14.0 (q). | 272 (<1), 239 (7), 195 (17), 137 (45), 124 (27), 59 (94), 45 (100). |
| 4 | 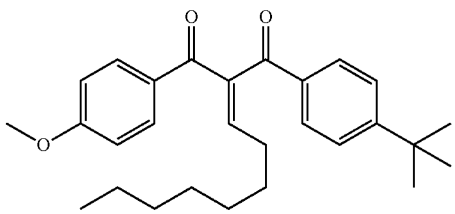 [SMILES: CCCCCCC/C=C(/C(=O)c1ccc(OC)cc1)C(=O)c1ccc(C(C)(C)C)cc1] | (purified by chromatography) | 194.1 (s), 192.8 (s), 163.9 (s), 156.2 (s), 147.9 (d), 141.9 (s), 133.3(s), 131.7 (d), 130.3 (s), 129.5 (d), 125.4 (d), 13.7 (d), 55.5 (q), 35.1 (s), 31.6 (t), 31.1 (q), 31.0 (t), 31.0 (t), 29.2 (t), 28.9 (t), 22.5 (t), 14.0 (q). | 420 (24, M$^+$), 363 (95), 335 (39), 279 (36), 255 (35), 161 (91), 150 (97), 135 (100). |
| 5 | 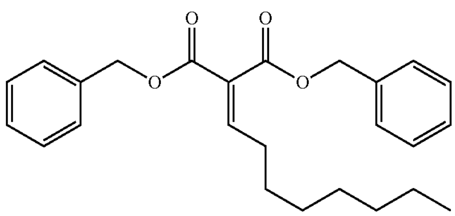 [SMILES: CCCCCCCC=C(C(=O)OCc1ccccc1)C(=O)OCc1ccccc1] | (purified by chromatography) | 165.3 (s), 163.8 (s), 151.1 (d), 135.6 (s), 135.4 (s), 128.5 (d), 128.4 (d), 128.3 (d), 128.2 (d), 128.0 (d), 128.0 (d), 67.0 (t), 66.9 (t), 31.7 (t), 29.9 (t), 29.2 (t), 28.9 (t), 28.3 (t), 22.6 (t), 14.1 (q). | 394 (5, M$^+$), 200 (16), 197 (20), 179 (77), 123 (15), 109 (12), 91 (100). |
| 6 | 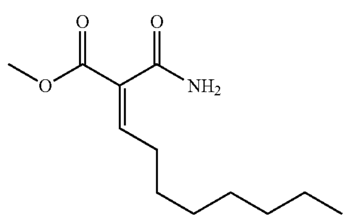 [SMILES: CCCCCCC/C=C(\C(N)=O)C(=O)OC] | (purified by chromatography) | 166.8 (s), 166.2 (s), 155.3 (d), 127.3 (s), 52.3 (q), 31.6 (t), 30.4 (t), 30.0 (t), 29.2 (t), 28.9 (t), 22.6 (t), 14.0 (q). | 227 (3, M$^+$), 210 (19), 178 (39), 168 (37), 153 (62), 139 (65), 113 (92), 81 (93), 41 (100). |
| 7 | 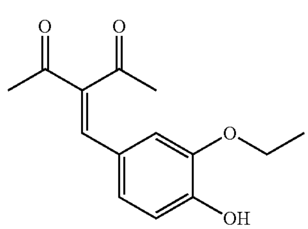 [SMILES: CCOc1cc(C=C(C(C)=O)C(C)=O)ccc1O] | (purified by chromatography) m.p. 126-128° C. | 206.4 (s), 196.4 (s), 148.4 (s), 146.0 (s), 140.6 (s), 140.1 (d), 125.0 (s), 125.0 (d), 114.9 (d), 112.2 (d), 64.6 (t), 31.7 (q), 26.3 (q), 14.7 (q). | 248 (30, M$^+$), 233 (8), 219 (4), 205 (11), 191 (11), 177 (11), 163 (25), 145 (11), 43 (100). |
| 8 | 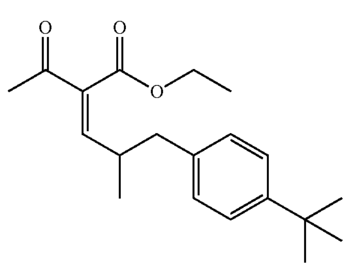 [SMILES: CCOC(=O)/C(=C\C(C)Cc1ccc(C(C)(C)C)cc1)C(C)=O] | (purified by chromatography, only Z-isomer described) | 201.2 (s), 164.4 (s), 152.3(d), 149.2 (s), 136.3 (s), 134.9 (s), 128.9 (d), 125.2 (d), 61.1 (t), 42.4 (t), 36.5 (d), 34.4 (s), 31.3 (q), 30.5 (q), 19.9 (q), 14.1 (q). | 316 (<1, M$^+$), 298 (3), 270 (8), 147 (100). |

| N° | Structure | b.p. (if distilled) [° C./mbar] | 13C-NMR CDCl3, 100 MHz (only main isomer) | MS EI, 70 eV |
|---|---|---|---|---|
| 9 | (structure) | (purified by chromatography) | 165.4 (s), 164.1 (s), 152.9 (d), 152.6 (d), 148.9 (s), 135.8 (s), 135.6 (s), 129.0 (d), 128.8 (d), 128.7 (d), 128.6 (d), 128.2 (d), 127.8 (d), 127.7 (d), 125.2 (d), 76.2 (d), 61.1 (t), 41.6 (t), 41.6 (t), 41.2 (s, 1 C), 41.1 (t), 39.1 (t), 39.0 (t), 38.3 (d), 38.2 (d), 38.2 (d), 36.1 (d), 35.8 (d), 34.3 (s), 33.5 (q), 33.4 (q), 31.3 (q), 30.5 (s), 30.5 (s), 30.4 (s), 28.3 (t), 28.3 (t), 24.5 (q), 21.9 (t), 21.9 (t), 19.1 (q), 18.9 (q), 17.1 (q), 17.0 (q), 14.1 (q) | 456 (2, M+), 318 (7), 300 (11), 147 (100). |
| 10 | (structure) | (purified by chromatography) | (only E-isomer described) 195.0 (s), 166.3 (s), 149.1 (s), 146.8 (d), 145.3 (s), 137.6 (s), 128.5 (d), 125.1 (d), 124.5 (d), 123.9 (d), 61.1 (t), 39.5 (d), 38.3 (t), 34.1 (d), 26.8 (q), 24.0 (q), 21.6 (q), 14.1 (q). | 302 (<1, M+), 256 (9), 228 (5), 213 (5), 172 (9), 147 (100), 105 (20), 91 (14). |
| 11 | (structure) | (purified by chromatography) | (mixture of E and Z-isomers) 201.2 (s), 195.1 (s), 166.6 (s), 164.5 (s), 153.6 (d), 153.4 (d), 135.8 (s), 134.4 (s), 61.1 (t), 61.1 (s), 36.5 (t), 36.5 (t), 34.9 (d), 34.0 (d), 31.8 (t), 31.3 (t), 29.6 (t), 29.5 (t), 29.4 (t), 29.2 (t), 27.4 (t), 27.3 (t), 26.8 (q), 22.6 (t), 20.1 (q), 19.8 (q), 14.1 (q), 14.1 (q), 14.0 (q). | 296 (<1, M+), 281 (2), 250 (71), 151 (42), 143 (26), 137 (50), 124 (18), 43 (100). |
| 12 | (structure) | (purified by chromatography) | 165.7 (s), 164.0 (s), 154.2 (d), 127.3 (s), 61.1 (t), 61.1 (t), 36.4 (t), 34.7 (d), 31.8 (t), 29.5 (t), 29.5 (t), 29.2 (t), 27.3 (t), 22.6 (t), 19.8 (q), 14.1 (q), 14.0 (q). | 326 (<1, M+), 311 (<1), 297 (<1), 281 (23), 253 (4), 234 (100), 199 (9), 173 (59), 160 (62), 141 (41), 122 (85), 108 (86). |

(*) The product contains ca. 15% of 2-(1-hydroxy-ethylidene)-dec-3-enoic acid 2-(2-methoxy-ethoxy)-ethyl ester. The starting material, 3-oxo-butyric acid 2-(2-methoxy-ethoxy)-ethyl ester, is prepared as follows:

Ethyl acetoacetate (39.0 g, 0.30 mol) and diethyleneglycol monomethyl ether (36.0 g, 0.30 mol) are heated to 110° C. (oil bath temperature) and tetraisopropyl orthotitanate (0.60 ml, 2.0 mmol, 0.7 mol %) is added. The temperature is further increased to 150° C. After 30 min methanol (5 g) is distilling off and collected. The temperature is maintained for further 8 h while lowering the pressure in the apparatus to 800 mbar. After cooling to room temperature, the residue is distilled at 65-120° C./0.06 mbar to isolate 30.5 g of product containing ca. 10% of diethyleneglycol monomethyl ether (yield 44%).

13C-NMR (CHCl13, 100 MHz): 200.4 (s), 167.0 (s), 89.9 (d), 71.8 (t), 70.4 (t), 68.8 (t), 64.2 (t), 59.0 (q), 50.0 (t), 30.0 (q).

MS (EI, 70 eV): 302 (<1, M+), 257 (2), 217 (10), 199 (15), 186 (15), 171 (4), 157 (13), 105 (100).

EXAMPLE 13

Application in Fabric Softener

To each of two samples of a standard unperfumed fabric softener base of the ester quat type is added one of the following:
1) 0.20% wt/wt of 2-methylundecenal
2) 0.32% wt/wt of ethyl 2-acetyl-4-methyltridec-2-enoate (Example 11), equivalent to 0.20% wt/wt of 2-methylundecanal.

These bases are then added to the rinse cycle of a washing machine loaded with cotton terry towels. After centrifugation, the towels are evaluated olfactorily by a panel of trained evaluators. Odour scores are attributed to each towel at the given time, which are as follows: 0 (odourless), 1 (very weak), 2 (weak), 3 (medium), 4 (strong) and 5 (very strong). The arithmetic means of the scores from all evaluators are reported in the following table.

|  | 2-methylundecanal | ethyl 2-acetyl-4-methyltridec-2-enoate |
|---|---|---|
| wet | 5 | 2.1 |
| 1 d | 0.3 | 3.6 |
| 2 d | 0.9 | 4 |
| 6 d | 0.3 | 3.8 |

From day 1 to day 6, the towel washed with the fabric softener base containing a compound according to the invention exhibits a strong 2-methylundecanal note, whereas the towels washed with base containing the free aldehyde are almost odourless.

EXAMPLE 14

Application in Liquid Detergent

To each of four samples of a standard unperfumed heavy duty liquid detergent base samples is added one of the following:
1) 0.20% wt/wt of 2-methylundecenal
2) 0.32% wt/wt of ethyl 2-acetyl-4-methyltridec-2-enoate (Example 11), equivalent to 0.20% wt/wt of 2-methylundecanal.
3) 0.20% wt/wt of 3-(3-isopropylphenyl)butanal
4) 0.32% wt/wt of ethyl 2-acetyl-5-(3-isopropylphenyl)hex-2-enoate (Example 10), equivalent to 0.20% wt/wt of 3-(3-isopropylphenyl)butanal)

Four individual 40° C. wash cycles are performed with the above samples, each with a load of cotton terry towels. Odour scores are attributed to the individual towels after time intervals by a panel of trained evaluators as described in example 3. The results are shown in the following table:

|  | 2-methylundecanal ("Aldehyde C12MNA") | ethyl 2-acetyl-4-methyltridec-2-enoate | 3-(3-isopropylphenyl)-butanal ("Florhydral") | 2-acetyl-5-(3-isopropylphenyl)-hex-2-enoate |
|---|---|---|---|---|
| wet | 3.6 | 1.5 | 2.3 | 3.5 |
| 1 d | 0 | 2.3 | 1.0 | 2.8 |
| 2 d | 0 | 2.3 | n.d. | n.d. |
| 3 d | 0 | 2.4 | n.d. | n.d. |

From wet to day 3, the towels washed with the liquid detergent base comprising a compound according to the invention exhibit a strong 2-methylundecanal note, whereas the towels washed with base containing the free aldehyde are almost weak to odourless. Likewise, the towels washed with 2-acetyl-5-(3-isopropylphenyl)hex-2-enoate exhibit a strong Florhydral note after 1 day on the dry towel, whereas the towel washed with free Florhydral has only a very weak smell.

EXAMPLE 15

Determination of Urine Malodour Reduction in Presence of Precursor

Preparation of Samples: 30g of sand was dosed with 0.25% of one of the following (0.004 g of 2-methylundecanal "Aldehyde C12 MNA" for Sample 2 and 0.075g of ethyl 2-acetyl-4-methyltridec-2-enoate for Sample 3). Next 5 g of inoculated cat urine was added to the sand and left at room temperature. The urine malodour and fragrance intensity were assessed daily for 6 days.

Testing procedure: The samples were contained in 120 g powder clear glass jars with lids. The test samples were assessed by a group of trained panellists (consisting of 5 individuals). The malodour intensity and fragrance intensity were rated using the Labeled Magnitude Scale (LMS). Mean ("Malodour Intensity" and "Fragrance Intensity") and standard error of the mean ("SE") were obtained, where 0 represents "No Sensation" and 100 represents "The Strongest Imaginable Sensation".

| No. | Group | Time | Malodour Intensity | SE | Fragrance Intensity | SE |
|---|---|---|---|---|---|---|
| 1 | Sand + Inoculated Cat Urine (Control) | 3 hrs | 83 | 3.391 | 0 | 0.000 |
|  |  | 24 hrs | 68.2 | 3.353 | 0 | 0.000 |
|  |  | 48 hrs | 86 | 2.915 | 0 | 0.000 |
|  |  | 72 hrs | 88.75 | 6.575 | 0 | 0.000 |
|  |  | 144 hrs | 90 | 4.564 | 0 | 0.000 |
| 2 | Sand + Inoculated Cat Urine + Aldehyde C12 MNA | 3 hrs | 82 | 2.708 | 0 | 0.000 |
|  |  | 24 hrs | 67 | 5.831 | 20 | 12.247 |
|  |  | 48 hrs | 71 | 5.788 | 12 | 12.000 |
|  |  | 72 hrs | 66.25 | 8.985 | 0 | 0.000 |
|  |  | 144 hrs | 71.25 | 7.739 | 0 | 0.000 |
| 3 | Sand + Inoculated Cat Urine + Precursor | 3 hrs | 42.5 | 4.787 | 43.75 | 15.326 |
|  |  | 24 hrs | 54 | 10.654 | 25.6 | 15.728 |
|  |  | 48 hrs | 43 | 9.950 | 34.6 | 14.288 |
|  |  | 72 hrs | 51.25 | 10.873 | 40 | 13.540 |
|  |  | 144 hrs | 58.75 | 6.575 | 25 | 8.660 |

The above table demonstrates that the precursor according to the present disclosure is effective in reducing the urine malodour while at the same time maintaining a long-lasting fragrance intensity from day 0 to day 6.

What is claimed is:

1. A composition comprising animal litter material and at least one compound of Formula I:

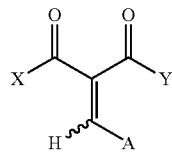

wherein
X is methyl, Y is oxyethyl, and
A is selected from

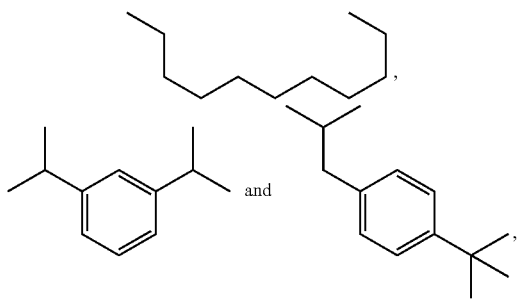

wherein the at least one compound of Formula I is present at a level effective to provide a reduced urine malodour effect.

2. The composition according to claim 1, wherein the compound of Formula I is ethyl 2-acetyl-5-(-4-(tert-butyl)phenyl)-4-methylpent-2-enoate.

3. The composition according to claim 1, wherein the compound of Formula I is ethyl 2-acetyl-5-(3-isopropylphenyl)hex-2-enoate.

4. The composition according to claim 1, wherein the compound of Formula I is ethyl 2-acetyl-4-methyltridec-2-enoate.

5. The composition according to claim 1, wherein the compound of Formula I is present at a level from about 0.05% to about 5% by weight of the litter material.

6. The composition according to claim 1, wherein the compound of Formula I is present at a level from about 0.1% to about 0.5% by weight of the litter material.

7. A method for reducing malodour impression on animal litter material comprising applying to the litter material from about 0.05% to about 5% by weight of the litter material, at least one compound of Formula I:

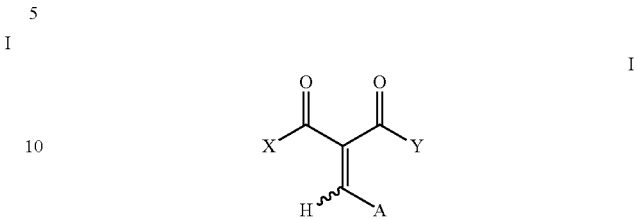

wherein
X is methyl, Y is oxyethyl, and
A is selected from

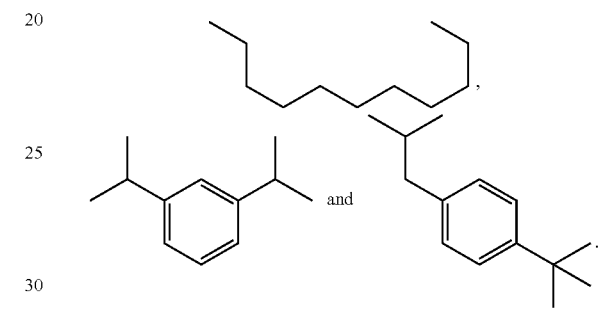

8. The method according to claim 7, wherein the compound of Formula I is ethyl 2-acetyl-5-(-4-(tert-butyl)phenyl)-4-methylpent-2-enoate.

9. The method according to claim 7, wherein the compound of Formula I is ethyl 2-acetyl-5-(3-isopropylphenyl)hex-2-enoate.

10. The method according to claim 7, wherein the compound of Formula I is ethyl 2-acetyl-4-methyltridec-2-enoate.

11. The method according to claim 7, comprising applying to the litter material from about 0.1% to about 0.5% by weight of the litter material, to the at least one compound of Formula I.

* * * * *